US010416083B2

(12) United States Patent
Signol et al.

(10) Patent No.: US 10,416,083 B2
(45) Date of Patent: Sep. 17, 2019

(54) METHOD AND KIT FOR DOSING IRON IONS IN LUBRICATING COMPOSITIONS

(71) Applicant: TOTAL MARKETING SERVICES, Puteaux (FR)

(72) Inventors: Catherine Signol, Colombes (FR); Luc Dargent, Bordeaux (FR); Gregory Mairot, Pompignac (FR); Thomas Debuissier, Salleboeuf (FR); Camille Demaille, Bordeaux (FR); Christian Baron, Limoges (FR)

(73) Assignee: TOTAL MARKETING SERVICES, Puteaux (FR)

( * ) Notice: Subject to any disclaimer, the term of this patent is extended or adjusted under 35 U.S.C. 154(b) by 145 days.

(21) Appl. No.: 15/541,914

(22) PCT Filed: Jan. 13, 2016

(86) PCT No.: PCT/EP2016/050523
§ 371 (c)(1),
(2) Date: Jul. 6, 2017

(87) PCT Pub. No.: WO2016/113281
PCT Pub. Date: Jul. 21, 2016

(65) Prior Publication Data
US 2017/0370851 A1     Dec. 28, 2017

(30) Foreign Application Priority Data

Jan. 14, 2015  (FR) ...................................... 15 50285

(51) Int. Cl.
*G01N 21/78*     (2006.01)
*G01N 33/28*     (2006.01)
(Continued)

(52) U.S. Cl.
CPC ......... *G01N 21/78* (2013.01); *G01N 33/2858* (2013.01); *G01N 33/2888* (2013.01); *G01N 33/30* (2013.01); *G01N 33/20* (2013.01)

(58) Field of Classification Search
CPC ........ G01N 21/78; G01N 33/20; G01N 33/28; G01N 33/2858; G01N 33/2888;
(Continued)

(56) References Cited

U.S. PATENT DOCUMENTS 3,506,403 A     4/1970 Fryer et al.
4,238,197 A    12/1980 Brooks et al.
(Continued)

FOREIGN PATENT DOCUMENTS

CN         101614656       12/2009
WO      2006/127098 A2    11/2006

OTHER PUBLICATIONS

Senee Kruanetr et al: "A Simple Flow Injection Spectrophotometric Determination of Iron Using Nitroso-R salt as complexing agent", J. Flow Injection Anal, vol. 24, Jan. 1, 2007 (Jan. 1, 2007), pp. 114-118, XP055248165.
(Continued)

Primary Examiner — Maureen Wallenhorst
(74) Attorney, Agent, or Firm — Young & Thompson

(57) ABSTRACT

Disclosed is a method for dosing iron ions, by spectrophotometry, especially ferric and ferrous ions, contained in a used lubricating composition, especially a lubricating composition of a marine engine. The invention also relates to a kit for implementing the method.

19 Claims, 2 Drawing Sheets

Figure 1:
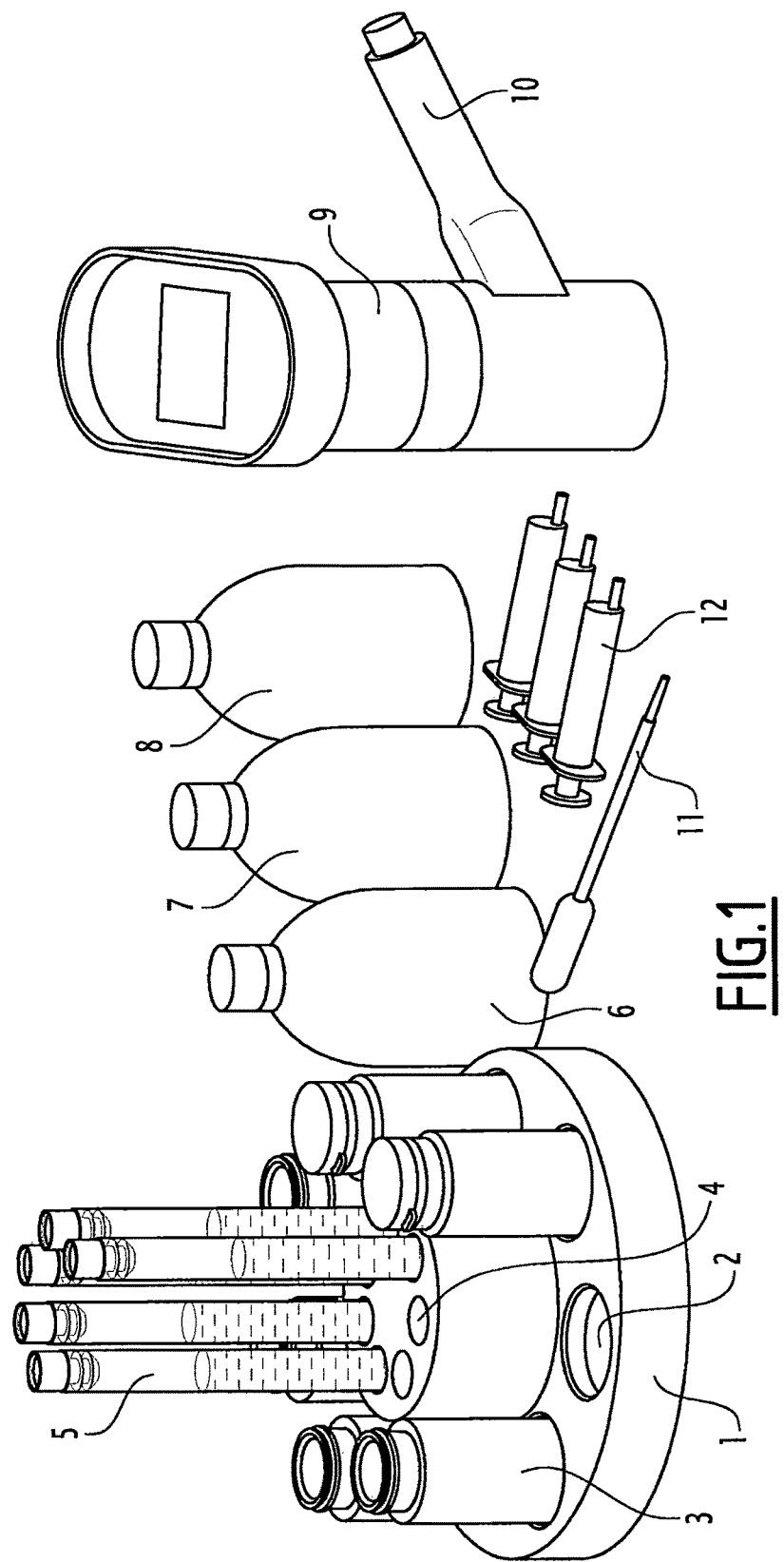

(51) Int. Cl.
*G01N 33/30* (2006.01)
*G01N 33/20* (2019.01)

(58) Field of Classification Search
CPC ............... G01N 33/30; Y10T 436/25; Y10T 436/25125; Y10T 436/255
USPC ..... 436/60, 73, 84, 164, 166, 171, 174, 175, 436/178; 422/82, 5, 82.09, 527
See application file for complete search history.

(56) References Cited

U.S. PATENT DOCUMENTS

| | | | | |
|---|---|---|---|---|
| 5,110,429 | A * | 5/1992 | Novotny | G01N 27/34 205/775 |
| 9,488,633 | B2 * | 11/2016 | Atkinson | G01N 31/22 |
| 2006/0270050 | A1 | 11/2006 | Naudts et al. | |
| 2009/0227035 | A1 * | 9/2009 | Naudts | B01L 3/502 436/60 |

OTHER PUBLICATIONS

Salvador A et al: "Determination of the total iron content of used lubricating oils by atomic-absorption with use of emulsions", Talanta, Elsevier, Amsterdam, NL, vol. 30, No. 12, Dec. 1, 1983 (Dec. 1, 1983), pp. 986-988, XP026596345, ISSN: 0039-9140, [retrieved on Dec. 1, 1983], DOI: 10.1016/0039-9140(83)80230-6.
International Search Report, dated Feb. 17, 2016, from corresponding PCT/EP2016/050523 application.
FR Search Report, dated Jul. 28, 2015, from corresponding FR 1550285 application.

* cited by examiner

METHOD AND KIT FOR DOSING IRON IONS IN LUBRICATING COMPOSITIONS

The present invention concerns a method for determining corrosive iron i.e. ferric and ferrous ions in lubricating compositions that are in-use, more particularly engine lubricating compositions in-use, more particularly marine engines. The present application also concerns a kit to implement this method.

Engines and in particular marine engines undergo major stresses when in use, in particular friction stresses, and are subjected to corrosion, especially marine engines for example due to the presence of sulfur in the fuel which converts to sulfuric acid during combustion. Lubricating compositions are generally used to reduce these stresses.

Through these phenomena, of friction and corrosion in particular, metal particles or contaminants particularly in iron particles, ferric ions and ferrous ions are released into these lubricating compositions. These metal contaminants, if present in too great an amount, can lead to changes in the properties of said lubricating compositions and hence in their performance becoming harmful for the engine (in particular shortened lifetime). It is therefore of advantage to determine these metal contaminants in lubricating compositions in order to determine the state of degradation of these compositions and thereby an optimal oil change time.

In addition, the assay of these metal contaminants also allows determination of the extent of these phenomena, particularly of friction and corrosion, and to take decisions regarding the maintenance and protection of the lubricated equipment, in particular by adjusting the quantity of lubricating composition to be added.

It is proposed by some laboratories to perform analyses of samples of in-use lubricating compositions to determine the amounts of metal contaminants. However, this requires the sending of samples, a lengthy implementation time and consequently delayed action.

It would therefore be advantageous to provide an iron assay method, in particular of ferric and ferrous ions resulting from corrosion in in-use lubricating compositions, and also a kit adapted for implementation of this method, that can be used in situ and are rapid and reliable.

Colorimetric assays exist whereby a range of iron concentration is determined visually by comparison with reference samples. However, these methods are scarcely reliable.

From WO2006127098 a method is also known to analyse the amount of iron contained in an in-use lubricating composition. However, with this method it is the total iron contained in said lubricating composition that is determined i.e. both particulate iron derived from friction phenomena and ferric and ferrous ions derived from corrosion. It is therefore not possible with this method to determine the true impact of each of these two phenomena taken separately, and for operators to take action accordingly.

It is therefore one of the objectives of the present invention to provide an «on-site» assay method to determine iron ions, ferric and ferrous ions—derived in particular from the corrosion of metal parts in engines—in lubricating compositions that are in-use recovered in particular under engine cylinders.

It is another objective of the present invention to provide said method, wherein the preparation of the sample for assay is quick and simple.

A further objective of the present invention is to provide said method that is quick to implement, preferably requiring less than 10 minutes, that is reliable and reproducible.

A further objective of the present invention is to provide a method allowing accuracy of measurement to within more or less 10 ppm and allowing measurement in the range of 0 to 900 ppm.

A further objective of the present invention is to provide a kit allowing the implementation of said method, that is quick and easy to use.

Other objectives will become apparent on reading the following description.

All these objectives are met by the present invention which proposes an «on-site» determination method of iron ions, particularly ferric and ferrous ions, in lubricating compositions and in-use lubricating compositions in particular e.g. recovered at the bottom of engine cylinders, via photochemical measurement after reaction of the iron ions with an iron ion complexing agent, the complexing reaction causing a change in colour that can be quantified by spectrophotometry.

The method of the invention to determine iron ions, in particular ferric and ferrous ions in lubricating compositions comprises the following steps:
a) Taking a sample of the lubricating composition to be analysed, e.g. at the bottom of the engine cylinders, in a first container;
b) Placing the first container containing the sample to be analysed on a magnet;
c) Adding to a second container:
   a first aqueous reactive composition CR1 comprising at least one extraction agent of ferric and ferrous ions from the oil phase to the aqueous phase;
   a second aqueous reactive composition CR2 comprising at least one reducing agent of ferric ions ($Fe^{3+}$) to ferrous ions ($Fe^{2+}$);
   a third reactive composition CR3 comprising at least one emulsion destabiliser; and
   a fourth reactive composition CR4 in an aqueous solution comprising a ferrous ion complexing agent, characterized in that this agent changes colour when complexed with ferrous ions;
   and mixing;
d) Optionally, photochemical measurement of the absorbance of the mixture obtained at step c);
e) Taking a few drops of lubricating composition contained in the first container, held in position on the magnet, and adding these few drops to the second container comprising the mixture of the first, second, third and fourth reactive compositions obtained at step c);
f) Agitating the mixture obtained at step e);
g) Conducting photochemical measurement of the absorbance of the mixture obtained at step f);
h) Determining the amount of ferrous ions in the lubricating composition on the basis of the measurements obtained at steps d) and g).

It is to be understood from step a) that it is the sample taken that is placed in a first container.

The lubricating composition to be analysed is preferably an in-use engine lubricating composition, preferably a lubricating composition for marine engine for example a ship engine or engine of a hydroelectric plant, etc. Preferably, the lubrication composition is a lubricating composition for a 2-stroke marine engine. Preferably, the lubricating composition to be analysed is an in-use lubricating composition collected at the bottom of engine cylinders.

The lubricating composition under consideration in the present invention comprises at least one lubricating base oil. In general, lubricating base oils may be oils of mineral, synthetic or vegetable origin, and mixtures thereof. The mineral or synthetic oils generally used belong to Groups I to V of the classification defined by API (or the equivalents thereof in the ATIEL classification) such as summarized below. The API classification is defined in: American Petroleum Institute 1509 "Engine oil Licensing and Certification System" 17$^{th}$ Edition, September 2012. The ATIEL classification is defined in: "The ATIEL Code of Practice", Number 18, November 2012.

|  | Saturates content | Sulfur content | Viscosity index |
| --- | --- | --- | --- |
| Group I Mineral oils | <90% | >0.03% | 80 ≤ VI < 120 |
| Group II Hydrocracked oils | ≥90% | ≤0.03% | 80 ≤ VI < 120 |
| Group III Hydrocracked or hydroisomerized oils | ≥90% | ≤0.03% | ≥120 |
| Group IV | PAO (Poly alpha olefins) | | |
| Group V | Esters and other bases not included in Group I to IV bases | | |

The Group I mineral oils can be obtained by distillation of selected naphthenic or paraffinic crudes followed by purification of the distillates obtained with processes such as solvent extraction, solvent or catalytic de-waxing, hydrotreatment or hydrogenation. The oils of Groups II and II are obtained by more elaborate purification processes e.g. a combination of treatments selected from among hydrotreatment, hydrocracking, hydrogenation and catalytic de-waxing. Examples of Group IV and V synthetic base oils include polyisobutenes, alkylbenzenes and polyalphaolefins such as polybutenes or esters.

In the lubricating compositions, the lubricating base oils can be used alone or in a mixture. For example, a mineral oil can be combined with a synthetic oil.

Cylinder oils for two-stroke marine engines are generally characterized by a viscosity grade of SAE-40 to SAE-60, generally SAE-50 equivalent to kinematic viscosity at 100° C. of between 16.3 and 21.9 mm$^2$/s measured as per standard ASTM D445. Grade SAE-40 oils have a kinematic viscosity at 100° C. of between 12.5 and 16.3 cSt measured as per standard ASTM D445. Grade SAE-50 oils have a kinematic viscosity at 100° C. of between 16.3 and 21.9 cSt measured as per standard ASTM D445. Grade SAE-60 oils have a kinematic viscosity at 100° C. of between 21.9 and 26.1 cSt measured as per standard ASTM D445. The lubricating compositions of the invention preferably have a kinematic viscosity measured as per standard ASTM D445 at 100° C. ranging from 12.5 to 26.1 cSt, preferably from 16.3 to 21.9 cSt. To obtain such viscosity, the lubricating compositions of the invention may also comprise one or more additives. Typically, a conventional formulation for marine engines, preferably two-stroke, is Grade SAE-40 to SAE-60, preferably SAE-50 (according to the SAE J300 classification) and comprises at least 40 by weight of a lubricating base oil of mineral or synthetic origin or mixtures thereof, adapted for use in a marine engine. For example, a Group I lubricating base oil, according to the API classification, can be used for the formulation of a cylinder lubricant. Group I lubricating base oils have a Viscosity Index (VI) ranging from 80 to 120; the sulfur content thereof is higher 0.03% and their content of saturated hydrocarbon compounds is lower than 90%.

The lubricating composition of the invention may also comprise an additive selected from among overbased detergents or neutral detergents. Detergents are typically anionic compounds having a long lipophilic hydrocarbon chain and hydrophilic head, the associated metal cation is typically a metal cation of an alkaline or alkaline-earth metal. The detergents are preferably selected from among the salts of alkaline or alkaline-earth metals (in particular preferably calcium, magnesium, sodium or barium) of carboxylic acids, sulfonates, salicylates, naphthenates, and phenate salts. These metal salts may contain the metal in an approximately stoichiometric amount relative to the anionic group(s) of the detergent. In this case, the term used is non-overbased or «neutral» detergents even though they also contribute some basicity. These «neutral» detergents typically have a BN (Base Number), measured as per standard ASTM D2896, of less than 150 mg KOH/g, or less than 100 mg KOH/g, or even less than 80 mg KOH/g of detergent. This type of so-called neutral detergent may partly contribute to the BN of lubricating compositions. Those employed are for example neutral detergents of the type alkaline and alkaline-earth metal carboxylates, sulfonates, salicylates, phenates, naphthenates e.g. calcium, sodium, magnesium, barium. If the metal is in excess (in an amount higher than the stoichiometric amount relative to the anionic group(s) of the detergent), we are dealing with so-called overbased detergents. They have a high BN, higher than 150 mg KOH/g of detergent, typically ranging from 200 to 700 mg KOH/g of detergent, preferably 250 to 450 mg KOH/g of detergent. The excess metal imparting the overbased nature to the detergent is in the form of oil-insoluble metal salts e.g. carbonate, hydroxide, oxalate, acetate, glutamate, preferably carbonate. In one same overbased detergent, the metals of these insoluble salts may or may not be the same as those in oil-soluble detergents. They are preferably selected from among calcium, magnesium, sodium or barium. Overbased detergents are therefore in the form of micelles composed of insoluble metal salts held in suspension in the lubricating composition by the detergents in the form of oil-soluble metal salts. These micelles may contain one or more types of insoluble metal salts, stabilised by one or more types of detergent. Overbased detergents comprising a single type of soluble detergent metal salt are generally designated according to the type of hydrophobic chain of this latter detergent. They are therefore designated as being of phenate, salicylate, sulfonate, naphthenate type depending on whether this detergent is respectively a phenate, salicylate, sulfonate, or naphthenate. Overbased detergents are designated as being of mixed type if the micelles comprise several types of detergents, differing from one another through the nature of their hydrophobic chain. The overbased detergent and neutral detergent can be selected from among carboxylates, sulfonates, salicylates, naphthenates, phenates, and mixed detergents associating at least two of these types of detergent. The overbased detergent and neutral detergent are particularly compounds containing metals selected from among calcium, magnesium, sodium or barium, preferably calcium or magnesium. The overbased detergent can be overbased with insoluble metal salts selected from the group of carbonates of alkaline and alkaline-earth metals, preferably calcium carbonate. The lubricating composition may comprise at least one overbased detergent and at least one neutral detergent such as defined above.

As mentioned in the foregoing, in one embodiment of the invention, the lubricating composition has a BN as determined by standard ASTM D-2896 of no more than 50, preferably no more than 40, advantageously no more than 30 milligrams of potash per gram of lubricating composition, ranging in particular from 10 to 30, preferably 15 to 30, advantageously 15 to 25 milligrams of potash per gram of lubricating composition. In this embodiment of the invention, it is possible that the lubricating composition does not comprise detergents containing alkaline or alkaline-earth metals, overbased with carbonate metal salts.

In another embodiment of the invention the lubricating composition has a BN determined in accordance with standard ASTM D-2896 of at least 50, preferably at least 60, more preferably at least 70, advantageously 70 to 100.

The lubricating composition may also comprise at least one other additional additive selected from among dispersants, anti-wear additives or any other functional additive. Dispersants are well-known additives used in the formulation of lubricating compositions, in particular for application in the marine sector. Their primary role is to hold in suspension the particles initially present or which occur in the lubricant throughout its use in the engine. They prevent agglomeration thereof by acting on steric hindrance. They may also have a synergic effect on neutralisation. The dispersants used as lubricant additives typically contain a polar group associated with a relatively long hydrocarbon chain generally having 50 to 400 carbon atoms. The polar group typically contains at least one nitrogen, oxygen or phosphorus element. Compounds derived from succinic acid are dispersants given particular use as lubricant additives. In particular, use is made of succinimides obtained by condensation of succinic anhydrides and amines, succinic esters obtained by condensation of succinic anhydrides and alcohols or polyols. These compounds can then be treated with various compounds, particularly sulfur, oxygen, formaldehyde, carboxylic acids and compounds containing boron or zinc to produce borated succinimides for example or zinc-blocked succinimides. Mannich bases, obtained by polycondensation of phenols substituted by alkyl groups, of formaldehyde groups and of primary or secondary amines are also compounds used as dispersants in lubricants. In one embodiment of the invention, the dispersant content may be 0.1% or higher, preferably 0.5 to 2%, advantageously from 1 to 1.5% by weight relative to the total weight of the lubricating composition. Anti-wear additives protect friction surfaces through the formation of a protective film adsorbed on these surfaces. The one most frequently used is zinc dithiophosphate or DTPZn. Various phosphorus-, sulfur-, nitrogen-, chlorine- and boron-containing compounds are also found in this category. There exists a wide variety of anti-wear additives but the category the most used is the category of phospho-sulfurized additives such as metal alkylthiophosphates, in particular zinc alkylthiophosphates, and more specifically zinc dialkyldithiophosphates or DTPZn. The preferred compounds have the formula $Zn((SP(S)(OR_1)(OR_2))2$ where $R_1$ and $R_2$ are alkyl groups preferably having 1 to 18 carbon atoms. DTPZn is typically contained in amounts of the order of 0.1 to 2% by weight relative to the total weight of the lubricating composition. Amine phosphates, polysulfides, in particular sulfurized olefins, are also frequently employed anti-wear additives. In lubricating compositions for marine engines, anti-wear and extreme-pressure additives are also usually found of nitrogen- or sulfur-containing type such as metal dithiocarbamates, particularly molybdenum dithiocarbamate. Glycerol esters are also anti-wear additives. Mention can be made for example of mono-, di- and tri-oleates, monopalmitates and monomyristates. In one embodiment, the content of anti-wear additives ranges from 0.01 to 6%, preferably 0.1 to 4% by weight relative to the total weight of the lubricating composition.

The other functional additives can be selected from among thickening agents, defoaming agents to counter the effect of the detergents, these possibly being polar polymers for example such as polymethylsiloxanes, polyacrylates, anti-oxidant and/or anti-rust additives e.g. organo-metallic detergents or thiadiazoles. These are known to persons skilled in the art. The weight content of these additives is generally 0.1 to 5 weight relative to the total weight of the lubricating composition.

Advantageously, in the method of the present invention step b) allows a deposit of particulate iron to be obtained at the bottom of the first container, that may be contained in the lubricating composition to be analysed, and resulting from friction of engine parts. Particularly advantageously, the sampling at step e) is performed on the supernatant which allows conducting of the assay solely on ferric and ferrous ions, and thereby to determine solely the extent of the corrosion phenomenon alone.

In the present invention by « iron ions » is meant ferric ions and ferrous ions.

Lubricating compositions are generally composed of lubricating oils and additives and are therefore viscous and coloured. It is therefore not easy to carry out colorimetric determination of iron ions directly in a lubricating composition. The present invention therefore proposes placing the iron ions in an aqueous phase. Advantageously, the first reactive composition (CR1) of the method of the present invention, in an aqueous solution, comprises at least one extracting agent of ferric and ferrous ions for extraction thereof from the oil phase of the lubricating composition towards the aqueous phase. The extracting agent allows all the ferric and ferrous ions to be moved from the oil phase of the lubricating composition to the aqueous phase, the water being provided in particular by composition CR1 in which complexing with the complexing agent and assay will take place. This extracting agent is particularly selected from among agents that solubilise ferric and ferrous ions that are immiscible in the lubricating composition. Among these extracting agents particular mention can be made of acids, preferably acids having a pKa of between −5 et +5, in particular sulfuric acid, nitric acid, hydrochloric acid, phosphoric acid, alone or in a mixture. Preferably the acid has a pKa of −3.

The composition CR1 may also comprise other constituents, in particular additives contributing towards the preparation of the composition and advantageously allowing the rapidity of analysis to be increased. Among these additives, mention can be made of co-solvents promoting solubilisation of the compounds of the reactive composition CR1, for example of alcohol type e.g. ethanol, 1,4-butanediol, preferably ethanol.

In the second reactive composition CR2 of the present invention, the reducing agent of ferric ions to ferrous ions is preferably selected from among the following reducing agents: hydroquinone, hydroxylamine hydrochloride, hydrazine, dithionite, alone or in a mixture.

With the reducing agent it is possible to obtain a solution solely comprising iron ions in a single form (entity) and thereby to obtain more reliable and accurate determination.

The composition CR2 may also comprise buffer solutions allowing the pH to be maintained substantially stable, preferably between 2 and 7, more preferably between 2 and 3. Among buffer solutions, mention can be made of base or acid solutions or mixtures thereof e.g. solutions, particularly concentrated, of a preferably weak acid and its conjugate base, salts e.g. sodium salts such as sodium acetate, or a mixture thereof. Preferably, the buffer solution is selected from among solutions of sodium acetate and an acid, in particular acetic acid, solutions of glycine and hydrochloric acid, solutions of ethanoic acid and sodium ethanoate, or solutions of citric acid and sodium phosphate. Preferably, the first reactive composition of the present invention comprises 1 to 10% by weight of extracting agent. Preferably, the second reactive composition of the present invention comprises 1 to 15% by weight of reducing agent.

Particularly advantageously, the first and second reactive compositions can be mixed in a single aqueous reactive composition CR1' which then comprises at least one extracting agent of ferric and ferrous ions from the oil phase towards the aqueous phase, the water being contributed in particular by composition CR1', and at least one reducing agent reducing the ferric ions ($Fe^{3+}$) to ferrous ions ($Fe^{2+}$). Preferably, the reactive composition CR1' comprises 1 to 15% by weight of reducing agent and 1 to 10% by weight of extracting agent. This reactive composition CR1' may also comprise other constituents, in particular additives facilitating preparation of the composition and advantageously allowing the rapidity of analysis to be increased. Among these additives, mention can be made of co-solvents promoting solubilisation of the compounds of the reactive composition CR1', for example of alcohol type e.g. ethanol or 1,4-butanediol, preferably ethanol and/or buffer solutions allowing a substantially stable pH to be maintained, preferably between 2 and 7, more preferably between 2 and 3; among buffer solutions, mention can be made of basic or acid solutions or a mixture thereof, for example solutions, particularly concentrated, of a weak acid and its conjugate base, salts for example sodium salts such as sodium acetate or a mixture thereof. Preferably, the buffer solution is selected from among solutions of sodium acetate and an acid, in particular acetic acid, solutions of glycine and hydrochloric acid, solutions of ethanoic acid and sodium ethanoate, or solutions of citric acid and sodium phosphate.

Preferably, the reactive composition CR1' of the invention comprises ethanol or 1,4-butanediol (preferably ethanol), sulfuric acid, hydroxylamine hydrochloride and sodium acetate in solution in water.

The third reactive composition CR3 of the method of the invention comprises at least one emulsion destabilising agent. The first, second and fourth reactive compositions and the reactive composition CR1' are aqueous compositions. In a mixture with the lubricating composition, these aqueous compositions may form an emulsion. The third reactive composition therefore advantageously allows the breaking-up of the emulsion obtained and thereby allows better phase separation. Therefore, the third reactive composition of the method of the invention advantageously facilitates and accelerates the changeover of the ferric and ferrous ions of the oil phase of the lubricating composition towards the aqueous phase provided by the first, second and fourth reactive compositions or by reactive composition CR1'. Advantageously, the destabilising agent is formed of a compound non-miscible in water. The destabilising agent of the invention is preferably selected from among primary or secondary alcohols (C4 to C10), alone or in a mixture. Preferably the destabilising agent of the invention is selected from among isoamyl alcohol, octan-1-ol, octan-2-ol, 1-heptanol, 2-ethyl-hexanol, 2-ethyl-butanol, alone or in a mixture, preferably isoamyl alcohol, octan-1-ol, octan-2-ol, alone or in a mixture, preferably isoamyl alcohol, 1-heptanol, 2-ethyl-hexanol, 2-ethyl-butanol, alone or in a mixture, preferably isoamyl alcohol.

Preferably, the third reactive composition of the method of the present invention comprises 20 to 100% by weight of emulsion destabilising agent.

The third reactive composition of the present invention may also comprise additives, for example if the flash point of the destabilising agent is too high; the third reactive composition of the invention may comprise co-solvents allowing the flash point of the composition to be reduced. Among these co-solvents, mention can be made of light petroleum distillates, preferably comprising less than 2% of aromatic compounds, such as hydrocarbons for example, preferably C9 to C16, e.g. C9 to C16 n-alkane, C9 to C16 isoalkane, C9 to C16 cyclic hydrocarbons.

The fourth reactive composition CR4 of the method of the present invention comprises a ferrous ion complexing agent. This complexing agent is selected from among agents complexing ferrous ions and the complexing of which causes a change in colour which can be detected by measuring the absorbance of the solution obtained using a spectrophotometer. The measured absorbance can then be related to the content of ferrous ions, and hence of iron ions, in the analysed example expressed in ppm. Preferably, this complexing agent is selected from among ferrozine, ferene, phenantroline and derivatives thereof e.g. bathophenantroline, bipyridine, thioglycolic acid, nitroso-R salt (sodium salt of 3-hydroxy-4-nitroso-2,7-naphthalenedisulfonic acid), potassium ferricyanide (potassium hexacyanoferrate (III)), 2,4,6-tripirydyl-s-triazine (TPTZ). Preferably the complexing agent is selected from among TPTZ, potassium ferricyanide or nitroso-R salt. Preferably, the complexing agent is nitroso-R salt.

Preferably, the fourth reactive composition comprises 0.5 to 5% by weight of complexing agent. Preferably, the reactive composition comprises 1% by weight of complexing agent.

The determination method of the present invention is a colorimetric assay method which measures of the absorbance of a solution obtained by complexing of the complexing agent with ferrous ions, using UV-visible spectrometry and a spectrophotometer, preferably an electronic spectrophotometer. The absorbance measurements at steps d) and g) are therefore carried out with a spectrophotometer, preferably an electronic spectrophotometer.

Measurement of absorbance by spectrophotometry is based on the Beer-Lambert law. An incident light of intensity I0 passes through the aqueous solution to be analysed, part of this light is absorbed by the solution and the resulting intensity I is transmitted through the solution. The absorbance (A) of the solution is then determined with the following equation:

$$A = \log\left(\frac{I0}{I}\right)$$

It is possible to relate absorbance with the concentration of ferrous ions in the solution by means of a calibration curve giving a straight line linking absorbance with ferrous ion concentration of a solution of known concentration. The electronic spectrophotometer is previously calibrated with this calibration curve and the measured absorbance allows determination of the quantity of ferrous ions in ppm in the sample to be analysed.

In a first embodiment, measurement of an absorbance blank can be performed on a container comprising the mixture of the four reactive compositions defined above. This blank measurement is then considered to be the spectrophotometer reference and each of the measurements made on the compositions obtained at step (f) is compared with this blank value to give the true absorbance value as explained below.

In a second embodiment, and to obtain a reliable, accurate value of absorbance and thereby indirectly the concentration of ferrous ions, a blank is obtained to take into account the influence of the second container and of the first, second, third and fourth reactive compositions on absorbance measurement. To do so, step d) to measure absorbance is conducted on the mixture obtained at step c) in the second container.

Using the difference between the absorbance obtained at step g) and that obtained at step c) the true absorbance of the solution obtained at step f) can be obtained, and it is thus possible to determine the corresponding quantity of iron ions. Particularly advantageously, the electronic spectrophotometer is programmed to calculate the difference between absorbances measured at steps d) and g) and thereby the corresponding concentration of iron ions in the solution to be analysed, in ppm.

At step g), the second container is placed in the spectrophotometer so that the emitted incident light passes solely through the aqueous phase. As will be seen below, the spectrophotometer preferably presents an adapted receiving area for the sample, preferably at an adapted angle so that the emitted incident light passes solely through the aqueous phase.

Particularly advantageously, all these steps d), g) and h) are performed directly by the electronic spectrophotometer which is programmed accordingly.

Preferably, the agitation at step f) is carried out by upturning the container at least 5 times, e.g. 10 times. After agitation, the container is placed directly in the spectrophotometer. Advantageously agitation is gentle agitation.

Preferably, measurement at step g) is performed in less than 10 minutes after placing the container in the spectrophotometer, preferably measurement is performed 5 minutes after placing the container in the spectrophotometer, this time representing the time needed for the complexing reaction of the complexing agent with the ferrous ions.

Preferably, the first, second, third and fourth reactive compositions are each added in a proportion of 5 to 10 ml to the second container. Preferably, the first, second, third and fourth reactive compositions are each added in a proportion of 5 ml to the second container.

Preferably, the third and fourth reactive compositions and composition CR1' are each added in a proportion of 5 to 10 ml to the second container. Preferably the third and fourth reactive compositions and composition CR1' are added in a proportion of 5 ml to the second container.

In another embodiment, the first, second and third reactive compositions can be contained in a single reactive composition CR that is previously prepared.

Preferably, 1 to 10 drops, preferably 3 drops i.e. about 0.075 g or 100 µl, of lubricating composition to be analysed are added at step e) to the second container.

The method of the present invention can be repeated as many times as there are samples to be analysed. In this case, there are as many first and second containers as lubricating compositions to be analysed. Particularly advantageously, if step d) is carried out, steps d) and g) must be performed for each sample to be analysed, one after the other, and not by conducting steps d) for each of the samples to be analysed and then steps g) for each of the samples to be analysed; the spectrophotometer is effectively preferably parameterized to compare each of the mixtures obtained after steps c) and f).

Particularly advantageously, the method of the present invention is reliable, it allows the determination of 0 to 900 ppm of iron in the samples, preferably 50 to 700 ppm.

Advantageously, the method of the invention is quick and simple and does not require particular knowledge by the operator. Advantageously, with the method of the invention it is possible to obtain a result on the amount of iron ions present in an in-use lubricating composition in less than 10 minutes and with accuracy to within more or less 10 ppm.

Particularly advantageously, the method of the present invention does not require heating of the samples to be analysed, or digestion of the particulate iron.

The present invention also concerns a kit to implement the above-described method. This kit comprises:

a first aqueous reactive composition CR1 comprising at least one extracting agent of ferric and ferrous ions from the oil phase of the lubricating composition towards the aqueous phase;

a second aqueous reactive composition CR2 comprising at least one reducing agent of ferric ions ($Fe^{3+}$) to ferrous ions ($Fe^{2+}$);

a third reactive composition CR3 comprising at least one emulsion destabilising agent;

a fourth reactive composition CR4 in an aqueous solution comprising a complexing agent of ferrous ions, characterized in that this agent changes colour when complexing with ferrous ions;

a spectrophotometer, preferably an electronic spectrophotometer;

optionally at least one first container;

at least one second container;

optionally a device D1 to take a sample of the lubricating composition to be analysed;

a device D2 to take up each of the first, second, third and fourth reactive compositions;

a magnetised support;

at least one device D3 to take a sample of a few drops of lubricating composition to be analysed at step e).

CR1, CR2, CR3 and CR4 are such as defined above.

The spectrophotometer, preferably an electronic spectrophotometer, comprises a light emitting device e.g. a light-emitting diode; a photoelectric sensor; a receiving area for the second container; absorbance data processing software for conversion to ferrous ion concentration in ppm. Preferably the receiving area for the second container is positioned at between 10 and 50 mm, preferably between 15 and 30 mm, e.g. 24 mm from the bottom of the second container and oriented at an angle 35 to 75°, preferably 50 to 70°, e.g. 60° to allow measurement of absorbance solely in the aqueous phase of the mixture obtained at step f) containing the coloured complex formed between the complexing agent and the ferrous ions.

Preferably, the first container is in plastic material or in glass, preferably in plastic material. It may optionally have a stopper. Preferably the kit comprises at least as many first containers as there are samples of lubricating composition to be analysed. Engines have between 4 and 14 cylinders, therefore there are at least between 4 and 14 samples of lubricating composition to be analysed at the same time (one sample of lubricating composition per cylinder). Preferably there is at least one first container, preferably there are between one and 50 first containers e.g. between 5 and 40 first containers.

Preferably, the second container is a container in the form of a tube provided with a stopper, preferably a test tube provided with a stopper. It may be in plastic material or in glass, preferably in glass. Preferably, the kit comprises as many second containers as there are samples of lubricating compositions to be analysed. The kit therefore comprises between 1 and 100 second containers e.g. between 10 and 80 second containers, e.g. 50 second containers.

The first and second containers may be containers in glass or plastic; they may be disposable or able to be cleaned. Preferably, in the invention the first and second containers are disposable.

Preferably, device D1 to sample the lubricating composition to be analysed is a syringe, preferably in disposable plastic material. The kit may comprise as many devices D1 as there are lubricating compositions to be analysed, preferably the kit comprises 1 to 100 devices D1, preferably 10 to 80, e.g. 50.

Preferably, each of devices D2 is a syringe, preferably in disposable plastic material. The kit may comprise 3 to 18 devices D2, preferably 3 to 6 devices D2.

Preferably, the magnetised support is a holder intended to receive the first container comprising the lubricating composition to be analysed and having a magnet in its bottom part. Preferably, the magnetised support is a rack comprising 1 to 50, preferably 7 positions to receive first containers. Preferably the magnetised support is in two parts, a lower part comprising the positions to receive first containers, each of the positions comprising a magnet, and an upper part comprising positions for the second containers, the positions of the lower part and the positions of the upper part preferably being placed facing each other for rapid, simple identification of the lubricating compositions to be analysed.

Preferably, the device D3 to take a few drops of lubricating compositing to be analysed at step e) is a pipette, preferably in disposable plastic material, or a positive-displacement micropipette e.g. of 100 μl, for example of Microman Gilson or Transferpettor Brand type. There may be at least as many devices D3 as lubricating compositions to be analysed. For example, the kit may comprise 1 to 50 devices D3, preferably 50 devices D3.

In particularly advantageous manner, the kit of the invention can be stowed in a box or case and is therefore easily transportable.

FIG. 1) illustrates a kit of the invention.

Figure 2:
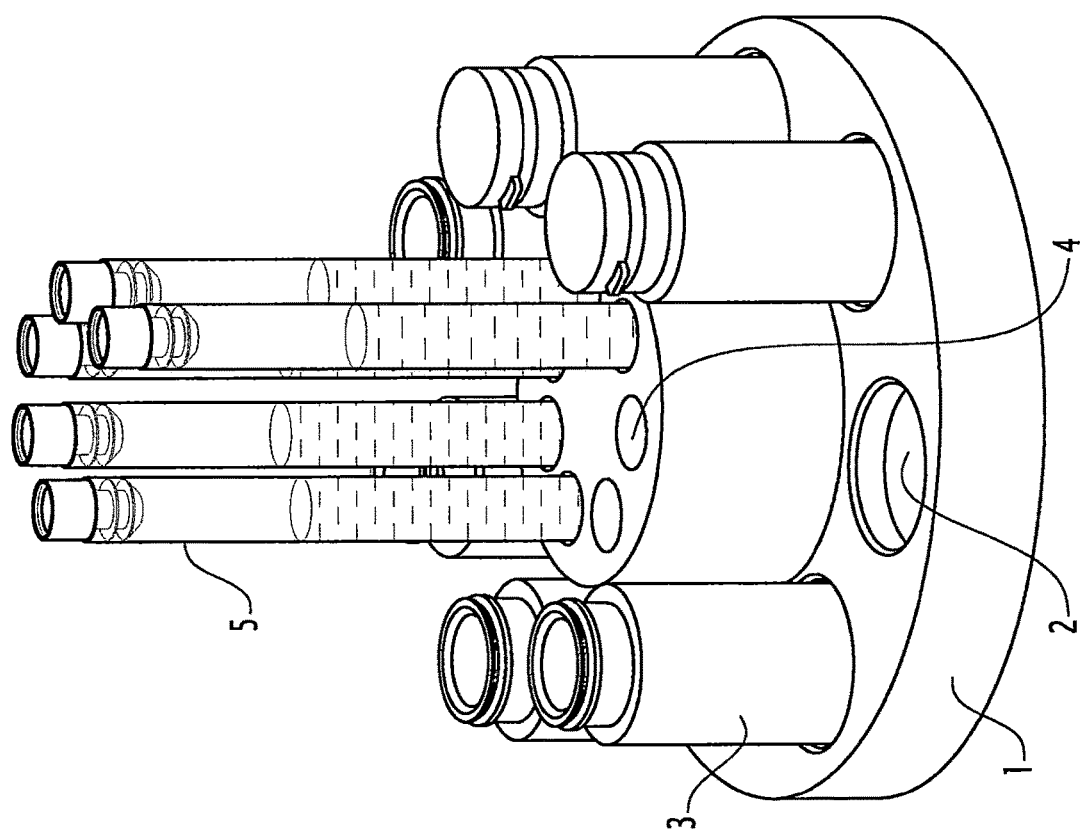

FIG. 2) illustrates a magnetised support of the invention.

The kit in FIG. 1) comprises:
- a magnetised support 1 comprising positions 2 each having a magnet and intended to receive first containers 3, and positions 4 intended to receive second containers 5;
- first containers 3;
- second containers 5;
- a reactive composition 6 (CR1');
- a reactive composition 7 (CR3);
- a reactive composition 8 (CR4);
- an electronic spectrophotometer 9 comprising a receiving area 10 to receive second containers, preferably this receiving area forms an angle of 35 to 75°, preferably 50 to 70° e.g. 60° with the body of the spectrophotometer;
- at least one device 11 (D3); and
- at least three devices 12 (D2).

FIG. 2 illustrates a magnetised support 1 comprising positions 2 each having a magnet and intended to receive first containers 3, and positions 4 intended to receive second containers 5.

The present invention will now be described with the aid of a non-limiting example of embodiment of the method and kit of the invention.

EXAMPLE

The operator sets the spectrophotometer in operation.

a) The operator collects the lubricating compositions to be analysed in first containers 3, and places these containers in positions 2 comprising magnets of the magnetised support 1, after which any particulate iron contained in the lubricating composition to be analysed is drawn downwards to the bottom of the container close to the magnet.

b) The operator then uses three separate devices 12 (D2) to place each of the reactive compositions 6 (CR1'), 7 (CR3) and 8 (CR4) in as many second containers 5 as there are oils to be analysed. The content of the second containers is mixed by upturning the second containers 5. All the second containers 5 are arranged at positions 4 of the magnetised support 1.

c) The operator then places one of the second containers 5 in the receiving area 10 of the spectrophotometer 9 and measures the absorbance of the solution contained in the second container 5.

d) This second container 5 is then replaced in one of the positions 4 of the magnetised support 1 and the operator, using a device 11 (D3), then adds thereto three drops of one of the lubricating compositions to be analysed contained in one of the first containers 3. To do so, the operator must take care not to insert the device D3 into the bottom of the container 3 to avoid taking up any particulate iron which may be present at the bottom of the container 3. After adding the lubricating composition, the operator records any change in colour resulting from the reaction between the iron ions and the complexing agent of the reactive composition CR4.

e) The container 5 is then agitated by turning it over 10 times, after which it is placed in the receiving area 10 of the spectrophotometer 9.

f) The container 5 is left 5 minutes in the receiving area 10 of the spectrophotometer 9 before initiating measurement of the absorbance of the solution contained in said second container 5.

g) The spectrophotometer calculates the difference between the absorbance measurement when container 5 only contains the reactive compositions CR1', CR3 and CR4, and the absorbance measurement when the lubricating composition is added to the container 5.

h) From the measurement obtained at g), the spectrophotometer determines the quantity of iron ions contained in the lubricating composition to be analysed.

Steps c) to h) are then repeated for each of the lubricating compositions to be analysed.

The invention claimed is:

1. Method for determining iron ions in a lubricating composition, comprising the following steps:
  a) Taking a sample of the lubricating composition to be analysed in a first container;
  b) Placing said first container containing the sample to be analysed on a magnet;
  c) Adding to a second container:
    a first aqueous reactive composition (CR1) comprising at least one extracting agent for extracting ferric and ferrous ions from an oil phase of the lubricating composition towards an aqueous phase of the lubricating composition formed by water in the first aqueous reactive composition (CR1) when the aqueous reactive composition (CR1) is added to the lubricating composition, wherein the ferric and ferrous ions are moved from the oil phase of the lubricating composition to the aqueous phase of the lubricating composition;
    a second aqueous reactive composition (CR2) comprising at least one reducing agent of ferric ions ($Fe^{3+}$) to ferrous ions ($Fe^{2+}$);
    a third reactive composition (CR3) comprising at least one emulsion destabilising agent; and a fourth reactive composition (CR4) in an aqueous solution comprising at least one complexing agent of ferrous ions, characterized in that this agent changes colour when complexing with ferrous ions;
and mixing thereof in order to form a mixture;

d) optionally, photochemical measurement of an absorbance of the mixture obtained at step c);

e) Taking drops of the lubricating composition contained in the first container, held in position on the magnet, and adding these drops to the second container comprising the mixture of the first, second, third and fourth reactive compositions obtained at step c);

f) Agitating the mixture obtained at step e);

g) Conducting photochemical measurement of an absorbance of the mixture obtained at step f); and h) determining a quantity of ferrous ions in the lubricating composition from the measurement obtained at step g) or if step d) is present, by subtraction of the measurement of step d) from the measurement of step g).

2. The method according to claim 1, wherein the at least one extracting agent is selected from among agents solubilising ferric and ferrous ions and being immiscible in the lubricating composition.

3. The method according to claim 2, wherein the at least one destabilising agent is selected from among primary or secondary alcohols having from 4 to 10 carbon atoms non-miscible in water, alone or in a mixture.

4. The method according to claim 1, wherein the at least one extracting agent is selected from among sulfuric acid, nitric acid, hydrochloric acid and phosphoric acid, alone or in a mixture.

5. The method according to claim 4, wherein the at least one extracting agent is sulfuric acid.

6. The method according to claim 5, wherein the a least one destabilising agent is selected from among primary or secondary alcohols having from 4 to 10 carbon atoms non-miscible in water, alone or in a mixture.

7. The method according to claim 4, wherein the at least one destabilising agent is selected from among primary or secondary alcohols having from 4 to 10 carbon atoms non-miscible in water, alone or in a mixture.

8. The method according to claim 1, wherein the at least one reducing agent of ferric ions to ferrous ions is selected from among hydroquinone, hydroxylamine hydrochloride, hydrazine and dithionite, alone or in a mixture.

9. The method according to claim 8, wherein the at least one reducing agent of ferric ions to ferrous ions is hydroxylamine hydrochloride.

10. The method according to claim 9, wherein the at least one destabilising agent is selected from among primary or secondary alcohols having from 4 to 10 carbon atoms non-miscible in water, alone or in a mixture.

11. The method according to claim 8, wherein the at least one destabilising agent is selected from among primary or secondary alcohols having from 4 to 10 carbon atoms non-miscible in water, alone or in a mixture.

12. The method according to claim 1, wherein the at least one destabilising agent is selected from among primary or secondary alcohols having from 4 to 10 carbon atoms non-miscible in water, alone or in a mixture.

13. The method according to claim 12, wherein the at least one destabilising agent is isoamyl alcohol, octan-1-ol, octan-2-ol, 1-heptanol, 2-ethyl-hexanol or 2-ethyl-butanol.

14. The method according to claim 13, wherein the at least one complexing agent is selected from among ferrous ion complexing agents and for which complexing is a cause of a change of colour able to be detected by spectrophotometric measurement of an absorbance of a mixture obtained at step e).

15. The method according to claim 14, wherein the at least one complexing agent is nitroso-R salt.

16. The method according to claim 1, wherein the at least one complexing agent is selected from among ferrozine, ferene, phenantroline and derivatives thereof, bipyridine, thioglycolic acid, nitroso-R salt (sodium salt of 3-hydroxy-4-nitroso-2,7-naphthalenedisulfonic acid), potassium ferricyanide, and 2,4,6-tripirydyl-s-triazine (TPTZ).

17. The method according to claim 1, wherein the first and second reactive compositions are included in an aqueous reactive composition CR1'.

18. Kit to implement the method according to claim 1, comprising:
a first aqueous reactive composition (CR1) comprising at least one extracting agent for extracting ferric and ferrous ions from an oil phase of the lubricating composition towards an aqueous phase of the lubricating composition formed by water in the first aqueous reactive composition (CR1) when the aqueous reactive composition (CR1) is added to the lubricating composition, wherein the ferric and ferrous ions are moved from the oil phase of the lubricating composition to the aqueous phase of the lubricating composition;
a second aqueous reactive composition (CR2) comprising at least one reducing agent of ferric ions ($Fe^{3+}$) to ferrous ions ($Fe^{2+}$);
a third reactive composition (CR3) comprising at least one emulsion destabilising agent;
a fourth reactive composition (CR4) in an aqueous solution comprising a ferrous ion complexing agent, wherein this agent changes colour when complexing with ferrous ions;
a spectrophotometer;
at least one second container;
a device (D2) to take up each of the first, second, third and fourth reactive compositions;
a magnetised support;
a first container; and
at least one device (D3) to take up drops of the lubricating composition located in the first container.

19. The kit of claim 18, further comprising at least one device (D1) to take a sample of lubricating composition to be analysed.

* * * * *